United States Patent [19]
Di Caprio et al.

[11] Patent Number: 6,123,712
[45] Date of Patent: Sep. 26, 2000

[54] BALLOON CATHETER WITH STENT SECUREMENT MEANS

[75] Inventors: Fernando Di Caprio, Mendota Heights; Stanley A. Nordin, Monticello; Louis G. Ellis, St. Anthony; Andrew J. Dusbabek, Dayton, all of Minn.

[73] Assignee: SciMed Life Systems, Inc., Maple Grove, Minn.

[21] Appl. No.: 08/916,610

[22] Filed: Aug. 22, 1997

Related U.S. Application Data

[63] Continuation-in-part of application No. 08/697,453, Aug. 23, 1996, abandoned.

[51] Int. Cl.[7] ................................................. A61F 11/00
[52] U.S. Cl. ........................ 606/108; 606/194; 604/101
[58] Field of Search .......................... 606/108, 192–198; 604/96, 101, 103

[56] References Cited

U.S. PATENT DOCUMENTS

| | | |
|---|---|---|
| 2,690,595 | 10/1954 | Raiche . |
| 4,271,839 | 6/1981 | Fogarty et al. . |
| 4,327,736 | 5/1982 | Inoue . |
| 4,403,612 | 9/1983 | Fogarty . |

(List continued on next page.)

FOREIGN PATENT DOCUMENTS

| | | |
|---|---|---|
| 0 266 957 | 10/1987 | European Pat. Off. . |
| 0 274 411 A2 | 7/1988 | European Pat. Off. . |
| 0 420 488 A1 | 4/1991 | European Pat. Off. . |
| 0 457 456 A1 | 11/1991 | European Pat. Off. . |
| 0 420 488 B1 | 4/1993 | European Pat. Off. . |
| 0 540 858 | 5/1993 | European Pat. Off. . |
| 0 582 870 A2 | 7/1993 | European Pat. Off. . |
| 0 582 870 A2 | 2/1994 | European Pat. Off. . |
| WO 92/08512 | 5/1992 | WIPO . |
| WO 92/19440 | 11/1992 | WIPO . |
| WO 95/09667 | 4/1995 | WIPO . |
| WO 95/22367 | 8/1995 | WIPO . |
| WO 96/04951 | 2/1996 | WIPO . |

OTHER PUBLICATIONS

Kim et al., Mechanical and Transport Properties of Coextruded Films, *Journal of Applied Polymer Science*, vol. 29, p. 2359–2382 (1984).

May et al., Polyvinyl and vinyl copolymers, *Modern Plastics Encyclopedia*, 1986–1987, p. 82.

Daniel O. Adams, BME, PTCA Balloon Materials, Their Characteristics and Impact on Catheter Selection, Sales training Technical Notes.

Tailoring Expansion Properties of Balloons for Medical Devices, *HealthWatch*, Prepared Oct. 25, 1994 at 3:04, p. 3.

Avanindra Jain et al., Effect of Inflation Pressures on Coronary Angioplasty Balloons, *The American Journal of Cardiology*, Jan. 1, 1986, vol. 57, p. 26–28.

Dialog Patent Search dated Nov. 3, 1994.

*Primary Examiner*—Michael Buiz
*Assistant Examiner*—Kevin Truong
*Attorney, Agent, or Firm*—Vidas, Arrett & Steinkraus, P.A.

[57] ABSTRACT

An assembly for delivery and deployment of an inflation expandable stent within a vessel is comprised of a catheter, and inflation expandable stent, an expandable balloon, and a securement means such as a corrugated tube component or an expandable tube component. The tube component is mounted on the inner shaft beneath the balloon and provides increased securement to the stent in a reduced delivery diameter to maintain the stent on the catheter during delivery to the deployment site. The tube component is adhered to the inner shaft and has a plurality of ribs or is fluid expandable to no more than the delivery diameter, and may be comprised of more than one separately inflatable pouch expandable to provide the stent with a substrate seat with increased friction and to decrease the slack in stent recoil crimping. The assembly is used in a method for delivering and deploying a stent, and also adds safety when loading/crimping the stent onto a balloon.

28 Claims, 5 Drawing Sheets

U.S. PATENT DOCUMENTS

| | | |
|---|---|---|
| 4,576,871 | 3/1986 | Oestreich . |
| 4,637,396 | 1/1987 | Cook . |
| 4,649,914 | 3/1987 | Kowalewski . |
| 4,702,252 | 10/1987 | Brooks et al. . |
| 4,763,645 | 8/1988 | Jang . |
| 4,787,388 | 11/1988 | Hofmann . |
| 4,820,349 | 4/1989 | Saab . |
| 4,885,194 | 12/1989 | Tight, Jr. et al. . |
| 4,932,958 | 6/1990 | Reddy et al. . |
| 4,983,167 | 1/1991 | Sahota . |
| 4,990,139 | 2/1991 | Jang . |
| 4,994,033 | 2/1991 | Shokey et al. . |
| 5,049,131 | 9/1991 | Deuss . |
| 5,057,092 | 10/1991 | Webster, Jr. . |
| 5,071,406 | 12/1991 | Jang . |
| 5,090,958 | 2/1992 | Sahota . |
| 5,096,848 | 3/1992 | Kawamura . |
| 5,108,370 | 4/1992 | Walinsky . |
| 5,195,969 | 3/1993 | Wang et al. . |
| 5,264,260 | 11/1993 | Saab . |
| 5,270,086 | 12/1993 | Hamlin . |
| 5,290,306 | 3/1994 | Trotta et al. . |
| 5,295,962 | 3/1994 | Crocker et al. .......................... 604/101 |
| 5,298,300 | 3/1994 | Hosoi et al. . |
| 5,304,132 | 4/1994 | Jang . |
| 5,304,135 | 4/1994 | Shonk . |
| 5,306,250 | 4/1994 | March et al. . |
| 5,342,305 | 8/1994 | Shonk . |
| 5,344,401 | 9/1994 | Radisch et al. . |
| 5,348,538 | 9/1994 | Wang et al. . |
| 5,358,487 | 10/1994 | Miller . |
| 5,415,635 | 5/1995 | Bagaoisan et al. . |
| 5,478,320 | 12/1995 | Trotta . |
| 5,490,839 | 2/1996 | Wang et al. . |
| 5,587,125 | 12/1996 | Roychowdhury . |
| 5,632,760 | 5/1997 | Sheiban et al. . |
| 5,776,099 | 7/1998 | Tremulis .................................. 606/194 |
| 5,836,965 | 11/1998 | Jendersee et al. . |

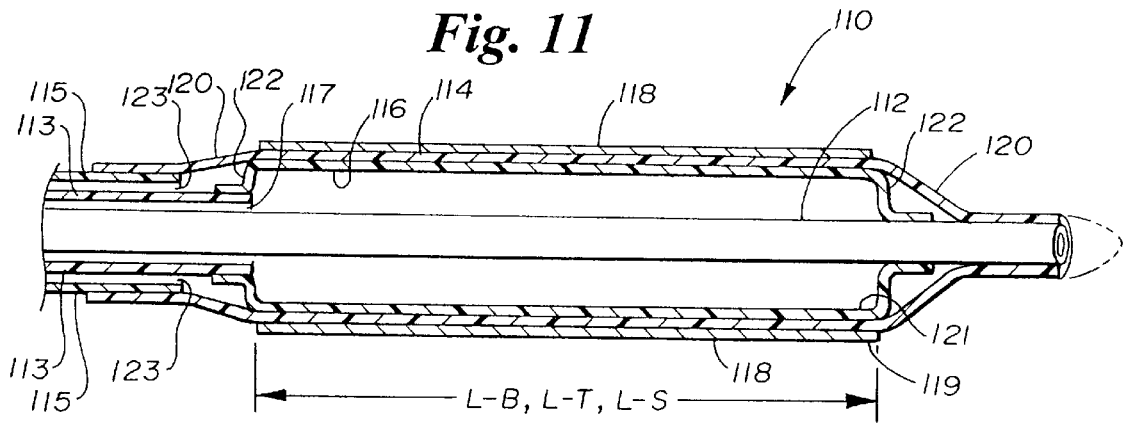
Fig. 11
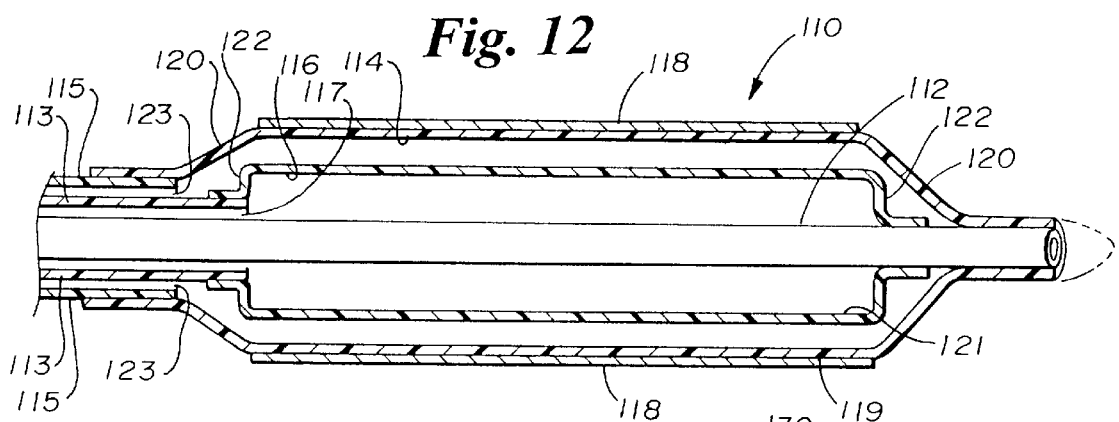
Fig. 12
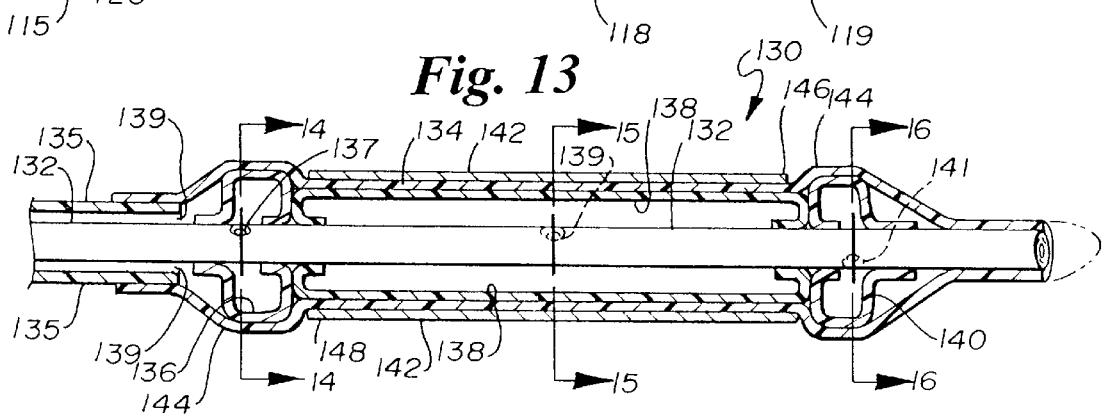
Fig. 13
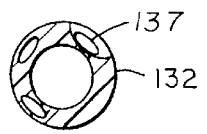    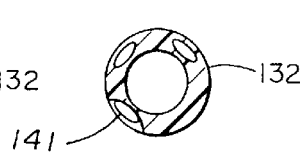
Fig. 14   Fig. 15   Fig. 16

BALLOON CATHETER WITH STENT SECUREMENT MEANS

REFERENCES TO CO-PENDING APPLICATIONS

This application is a continuation-in-part of application Ser. No. 08/697,453 filed Aug. 23, 1996 now abandoned entitled PRE-MOUNTED STENT DELIVERY DEVICE WITH INFLATABLE TUBE COMPONENT, herein incorporated by reference in its entirety.

BACKGROUND OF THE INVENTION

1. Field of the Invention

This invention relates to an assembly method for delivering and deploying an inflation expandable stent, particularly within a lumen of a body vessel. More specifically, this invention relates to the provision of a securement component positioned over the inner catheter, and beneath a balloon and a loaded stent, to maintain the stent on the catheter assembly during delivery to a stent deployment site.

2. Description of Relevant Art

Stents and stent delivery assemblies are utilized in a number of medical procedures and situations, and as such their structure and function are well-known. A stent is a general cylindrical prosthesis introduced via a catheter into a lumen of a body vessel in a configuration having a generally reduced diameter and then expanded to the diameter of the vessel. In its expanded configuration, the stent supports and reinforces the vessel walls while maintaining the vessel in an open, unobstructed condition.

Both self-expanding and inflation expandable stents are well-known and widely available. Self-expanding stents must be maintained under positive external pressure in order to maintain their reduced diameter configuration during delivery of the stent to its deployment site. Inflation expandable stents (also known as balloon expandable stents) are crimped to their reduced diameter about the delivery catheter, positioned at the deployment site, and then expanded to the vessel by diameter by fluid inflation of the balloon positioned between the stent and the delivery catheter. The present invention is particularly concerned with enhanced stent securement and safer stent loading in the delivery and deployment of balloon expandable stents.

In angioplasty procedure, there may be restenosis of the artery, which either necessitates another angioplasty procedure, a surgical bi-pass procedure, or some method of repairing or strengthening the area. To prevent restenosis and strengthen the area, a physician can implant an intravascular prosthesis for maintaining vascular patency, i.e. a stent, inside the artery at the lesion. The stent is expanded to a larger diameter for placement in the vasculature, often by the balloon portion of the catheter. Stents delivered to a restricted coronary artery, expanded to a larger diameter as by a balloon catheter, and left in place in the artery at the site of a dilated lesion are shown in U.S. Pat. No. 4,740,207 to Kreamer; U.S. Pat. No. 5,007,926 to Derbyshire; U.S. Pat. No. 4,733,665 to Palmaz; U.S. Pat. No. 5,026,377 to Burton et al.; U.S. Pat. No. 5,158,548 to Lau et al.; U.S. Pat. No. 5,242,399 to Lau et al.; U.S. Pat. No. 5,344,426 to Lau et al.; U.S. Pat. No. 5,415,664 to Pinchuck; U.S. Pat. No. 5,453,090 to Martinez et al.; U.S. Pat. No. 4,950,227 to Savin; U.S. Pat. No. 5,403,341 to Solar; U.S. Pat. No. 5,108,416 to Ryan et al.; and European Patent Application No. 707837A1 to Scheiban, all of which are incorporated herein by reference. A stent particularly preferred for use with this invention is described in PCT Application No. 96/03092-A1, published Feb. 8, 1996, the content of which is incorporated herein by reference.

In advancing a balloon expandable stent through a body vessel to the deployment site, there are a number of important considerations. The stent must be able to securely maintain its axial position on the delivery catheter. The stent, particularly its distal and proximal ends, are sometimes protected to prevent distortion of the stent, and minimize trauma to the vessel walls. Balloon expandable stent delivery and deployment assemblies are known which utilize restraining means that overlay the stent during delivery. U.S. Pat. No. 4,950,227 to Savin et al., relates to a balloon expandable stent delivery system in which a sleeve overlaps the distal or proximal margin (or both) of the stent during delivery. During inflation of the stent at the deployment site, the stent margins are freed of the protective sleeve(s) and the sleeves then collapse toward the delivery catheter for removal. A number of balloon expandable stent delivery and deployment assemblies do not use overlaying restraining members, such as the Savin sleeves, to position the stent for delivery. European Patent Application No. EP 055 3960A1 to Lau et al., uses an elastic sheath interspaced between the balloon and the stent. The sheath is said to act as a barrier to protect the balloon from the stent, allow uniform stent expansion, decrease balloon deflation time, prevent undesirable balloon flattening upon deflation and provide a friction substrate for the stent. The Lau sheath can be positioned on the inside or outside of the balloon. U.S. Pat. No. 5,409,495 to Osborne, similarly uses an elastic sleeve or sheath surrounding and in contact with the balloon for controlling the balloon radial expansion. In addition, Osborne is said to use restraining bands or a pair of balloons to achieve controllable stent expansion characteristics. U.S. Pat. No. 5,403,341 to Solar, relates to stent delivery and deployment assembly which uses a retaining sheath positioned about opposite ends of the compressed state. The retaining sheaths of Solar are adapted to tear under pressure as the stent is radially expanded, thus releasing the stent for engagement with the sheaths. U.S. Pat. No. 5,108,416 to Ryan et al. describes a stent introducer system which uses one or two flexible end caps and annular socket surrounding the balloon to position the stent during introduction to the deployment site. The content of all of these patents is incorporated herein by reference.

In positioning a balloon expandable stent on the delivery catheter over the fluid expandable balloon, the stent must be smoothly and evenly crimped to closely conform to the overall profile of the catheter and the unexpanded balloon. It has been noted that, due to physical properties of the material used in manufacturing the stent (stainless steel, tantalum, platinum or platinum alloys, or shape memory alloys such as Nitinol™) there is a certain amount of "recoil" of the stent despite the most careful and firm crimping. That is the stent evidences a tendency to slightly open up from the fully crimped position and once the crimping force has been released. For example, in the typical stent delivery and deployment assembly, if the stent has been fully crimped to a diameter of approximately 0.0035", the stent has been observed to open up or recoil to approximately 0.0037". This phenomenon has been characterized as "recoil crimping". Due to recoil crimping to this slightly enlarged diameter, it can be understood that the stent tends to evidence a certain amount of looseness from its desired close adherence to the overall profile of the underlying catheter and balloon. That is, the stent tends to have a perceptible relatively slack fit in its mounted and crimped position. During delivery, the stent can thus tend to slip and dislocate from its desired position on the catheter or even become separate from the catheter, requiring further intervention by the physician.

Further, there is a possibility of damaging the balloon during the stent crimping as a result of pinching the balloon material between the metal stent and any metal (or protruding object) on the inner guide lumen (e.g. marker bands).

According to the present invention, a securement means such as a corrugated (accordion-type) tube is secured over the inner catheter beneath the balloon to compensate for the undesired looseness or slack that due to recoil crimping and to aid in securing the stent to the balloon, as well as protecting the balloon material from being sandwiched between the stent and any metal or protruding item which may be mounted on the inner shaft/guide wire lumen, for delivery of the stent. The corrugated tube provides additional volume for improved stent securement, i.e. more surface area to crimp onto, and also maintains flexibility. In addition, when metal marker bands are employed on the inner catheter, the tubing aids in preventing damage to the balloon during crimping/loading of the stent. The tubing, which may be inflatable, compensates for the perceptible looseness due to recoil crimping and secures the stent during tracking and delivery and provides a good friction fit to the stent and insures good contact between the stent and underlying balloon and catheter, instead of merely relying on the bulk of the flaccid balloon over the underlying catheter to hold the stent on. According to the present invention, the tubing component will compensate for slackness in the fit of the stent due to recoil crimping.

According to another embodiment of the present invention, the securement means is an expandable tube component positioned under the expandable balloon to compensate for this undesired looseness or slack fit due to recoil crimping and to aid in securing the stent to the balloon and the catheter for delivery. The expandable tube component and the expandable balloon are each provided with separate, individually controllable fluid inflation sources. Once the stent has been fully crimped to conform to the overall profile of the catheter, the expandable balloon, and the underlying expandable tube component, the tube component is inflated. The tube component is inflated to at least the limits of the elastic deformation of the fully crimped stent. It is desirable to slightly further inflate the tube component to a pressure at which the fully crimped stent just begins to plastically deform. That is, the tube component may be inflated to a point at which the stent is just barely beginning to provide resistance to the expansion of the tube component, which is also characterized as a point at which the stent just barely begins to expand beyond the crimped position (taking into consideration the recoil crimping phenomenon). The desired pressure to which the tube component is inflated is characterized as the "securement pressure". The application of securement pressure to the tube component compensates for the perceptible looseness due to recoil crimping and secures the stent during tracking and delivery. The application of securement pressure to the tube component provides a good friction fit to the stent and ensures good contact between the stent and the underlying balloon, "securement pressurized" tube component and catheter. The desired diameter of the stent upon the application of securement pressure to the tube component is characterized as the "delivery diameter", because in this condition the stent can safely, reliably and securely be delivered to the pre-selected position within a body vessel. Instead of merely crimping the stent onto the balloon and the underlying catheter and relying on the bulk of the flaccid balloon to hold the stent on, according to the present invention, the expandable tube component will compensate for slackness in the fit of the stent due to recoil crimping. Prior to inflation of the tube component to the securement pressure, the physician preparing the assembly may manually sense a looseness of the stent in its position. When the tube component has been inflated to the necessary securement pressure, the physician will manually sense that the stent is securely retained or "stuck" in position. The expandable tube component is designed and constructed to be expandable to no more than is necessary to compensate for recoil crimping and is incapable of overexpanding to provide the pressure needed to fully expand the stent to its deployment position.

There are a number of descriptions of catheters which use a pair of coaxial, at least partially coextensive balloons. U.S. Pat. No. 5,512,051 to Want et al., describes a slip layered balloon made of a plurality of layers with a low friction substance between the layers. During expansion the layers are able to slide relative to each other softening the balloon while maintaining its strength. U.S. Pat. No. 5,447,497 to Sogard et al., relates to s a dual layered balloon, in which one balloon is compliant and the other is non-compliant, so that the balloon assembly has a non-linear compliance curve. U.S. Pat. No. 5,358,487 to Miller, describes a balloon catheter having an outer balloon surrounding an inner balloon. The inner balloon has a maximum inflation diameter less than that of the outer balloon, so that, upon inflation, the inner balloon bursts at a certain diameter, allowing the outer balloon to be further expanded. U.S. Pat. No. 5,290,306 to Totta et al., relates to a balloon catheter with an outer elastomeric sleeve to provide the balloon with pin hole and abrasion resistance. U.S. Pat. No. 5,049,132 to Shaffer et al., describes a first balloon and a second balloon, each having separate inflation lumens, the second balloon having apertures for controlled administration of a medication therethrough. U.S. Pat. No. 4,608,984 and 4,338,942 to Fogarty, each relate to a catheter with an inner non-elastic balloon and an outer elastic balloon. In each patent, the outer balloon aids in collapse and retraction of the inner balloon. U.S. Pat. No. 4,328,056 to Snooks, describes a method of making a double cuffed endotracheal tube component. However, none of these references show, suggest or render obvious an inner balloon, in conjunction with an outer deployment inflatable balloon, to provide securement pressure to a compressed stent during delivery to a site within a body vessel.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

SUMMARY OF THE INVENTION

The present invention is an assembly for delivery and deployment of an inflation expandable stent within a vessel. The assembly comprises a catheter, an expandable balloon mounted on the catheter, a stent securement means mounted on the catheter beneath or within the balloon, and a stent mounted on the balloon. The catheter has proximal and distal ends. The stent is inflation expandable from a delivery diameter to a deployment diameter. The delivery diameter is reduced from the deployment diameter for conforming the stent to the catheter. The stent, in its delivery diameter, is coaxially mounted on the catheter near the catheter distal end. The expandable balloon is coaxially mounted on the catheter axially within the stent. The balloon is designed and adapted for expansion of the stent from the delivery diameter to the deployment diameter upon application of fluid deployment pressure to the balloon. The securement means may be corrugated tubing mounted and adhered coaxially onto the catheter and situated between the balloon and the catheter itself. Alternatively, the securement means may be an expandable tube component mounted on the catheter. The expandable tube component is coaxially mounted on the catheter, axially within the expandable balloon. The expandable tube component is designed and adapted for fluid expansion to provide a securement pressure to the stent in the delivery diameter to maintain the stent in position on the catheter during delivery to the deployment site. The expandable tube component is sized and constructed to be fluid expandable to no more than the delivery diameter. The expandable tube component or corrugated tube is essentially equal in length to the stent and the stent is positioned on the assembly essentially coextensive with the tube component. When the stent is crimped and loaded onto the balloon, the balloon is situated therefore between the stent and the securement means. The securement means is preferably essentially equal to the length of the stent and the stent is positioned on the assembly essentially co-extensive with the tube component. The present invention is particularly directed to improved arrangements for releasably attaching the stent to the catheter to facilitate delivery thereof. Generally, the stent is held in place upon the catheter by means of an enlarged body carried by the catheter shaft within the balloon to which the stent and the balloon are fitted, as by crimping. The securement means on the catheter effectively holds the stent in place, takes up the slack due to recoil and protects the balloon material from being damaged during crimping.

BRIEF DESCRIPTION OF THE FIGURES

FIG. 11 is a side profile section of an alternative embodiment showing a balloon expandable stent delivery and deployment assembly, with the stent crimped to delivery diameter onto the balloon, the underlying inflating tube component and the catheter and with the inflating tube component inflated to securement pressure.

FIG. 12 is a side profile section, similar to FIG. 11, with the balloon and the stent fully inflated to deployment diameter.

FIG. 13 is a side profile section showing an alternative embodiment of a balloon expandable stent delivery and deployment assembly, having a tube component formed in several sections.

FIGS. 14, 15 and 16 are cross-sectional views taken along lines 4—4, 5—5 and 6—6 of FIG. 13, respectively.

DETAILED DESCRIPTION OF THE INVENTION

Figure 1:
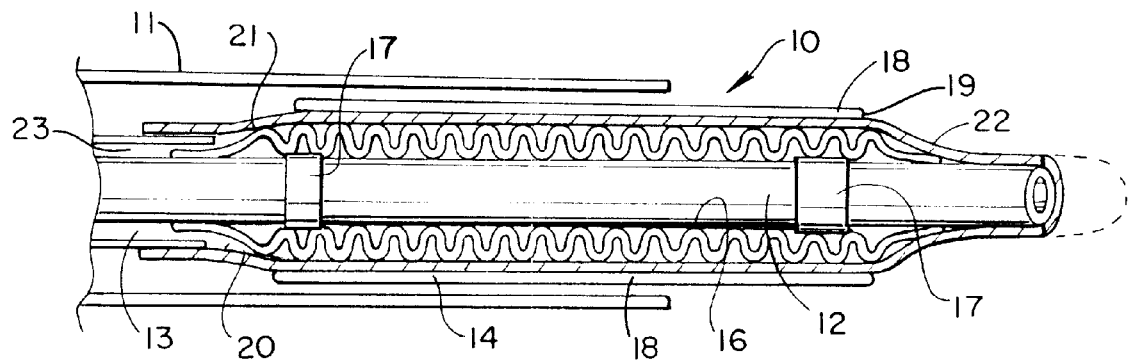
FIG. 1 is a side profile section showing a balloon expandable stent delivery and deployment assembly, with the stent crimped to delivery diameter onto the balloon, the underlying corrugated tube component and the catheter.
Figure 2:
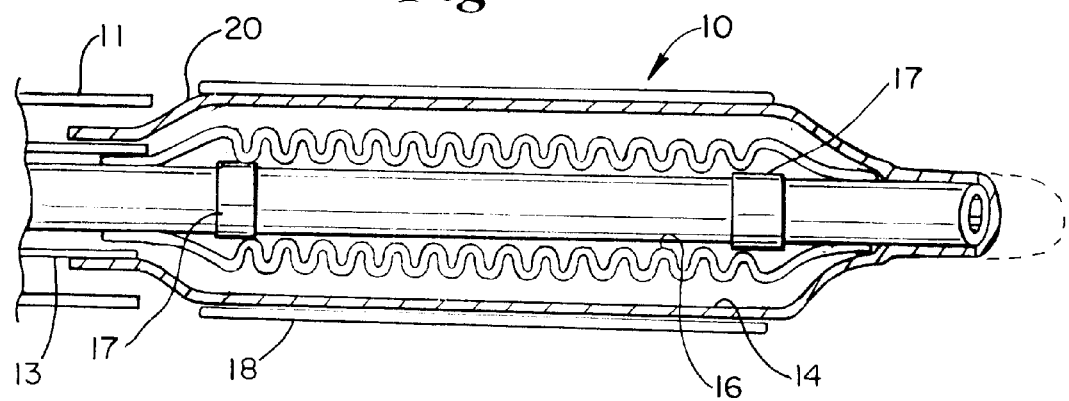
FIG. 2 is a side profile section, similar to FIG. 1, with the balloon and the stent fully inflated to deployment diameter.

FIGS. 1 and 2 illustrate a side profile section showing an inflation expandable stent delivery and deployment assembly, generally designated 10. Assembly 10 includes a catheter comprised of inner shaft 12 and outer shaft 13 of the coaxial type and an optional retractable delivery shaft 11 (typically called a guide catheter, shown retracted in FIG. 2), an inflation expandable balloon 14, a corrugated/ribbed stent securement device 16, optional marker bands 17 and an inflation expandable stent 18. Any conventional type of catheter may be used, such as a catheter of the type generally used for PTA or PTCA angioplasty procedures, for prostate therapy, and TTS endoscopic catheters for gastrointestinal use. However, coaxial types as show are most preferred. The particular catheters 12 and 13 shown are formed of a biocompatible and hydrophilic compatible material, such as a lubricous polyimide or poly ethylene. Other suitable materials for the catheters 12 and 13 include nylons, urethanes, and polypropylene materials compatible with coatings such as silicone and/or hydrophilic coatings. In addition to hydrophilic compatible materials, any biocompatible material may be used. For example, polyethylene or polypropylene can be coated with a hydrophilic material to render them hydrophilic compatible. Suitable catheters for use according to the present invention include a number of catheters available from SciMed Life Systems, Inc., Maple Grove, Minn., the assignee of the present invention, such as BANDIT™, COBRA™, VIVA™, VIVA PRIMO™, MAXXUM™, MAXXUM ENERGY™ and RANGER™ catheters.

Securement device 16 is fixed at its distal and/or proximal ends to inner shaft 12 at a position to be encompassed within the distal and proximal ends of the outer balloon 14. According to art-recognized convention, the length L-B of the balloon 14 is defined as the length of the body portion of the balloon 14, excluding the terminal cone sections 20. As seen in FIG. 2, the body portion of the balloon 14 is generally cylindrical when in its deployed or inflated condition. Securement device/tube component 16 is illustrated as having terminal sections 21,22. It is to be understood that, according to the present invention, either of the terminal sections 21, 22 may be relatively cone shaped, relatively vertical, relatively flat or of any other configuration known to those of skill in this art. A preferred length L-T of the tubing 16 is illustrated in FIGS. 1 and 2 as substantially equal to the length L-B of balloon 14, and substantially equal to the length L-S of stent 18. However, according to the present invention, stent 18 should be supported by the underlying tube component 16 for a length sufficient to permit accomplishment of the stated purpose of the tube component 16, to provide a superior securement and protective surface for stent 18 to maintain stent 18 in position with assembly 10 and to protect the balloon material during loading/crimping. It is also within the present invention for the tube component 16 to be slightly shorter than stent 18, for example, the distal end 19 of stent 18 may extend distally beyond the distal end 22 of tube component 16 (not shown), so that the distal end 19 of stent 18 can be crimped over the distal end 22 of tube component 16 to prevent the distal end 19 of stent 18 from catching and tending to snag or further open as it is maneuvered within a body vessel. As has been explained above, tube component 16 is designed and constructed to have enough flexibility and have enough volume to no more than is necessary to compensate for recoil crimping of stent 18 and to closely accommodate (or even slightly over stress) the delivery diameter of stent 18, taking into consideration the thickness of the intervening uninflated balloon 14. Typically, the tube component 16 will have a consistent frequency of ribs, but may also vary by having intermittent groups of ribs along the tubing.

The balloon and the crimped stent slightly conform to the undulations of the tube component for greater securement, but this conformation is not illustrated.

Tube component 16 may be formed from a thermoplastic material, preferably a low modulus polymer, such as Surlyn™, Pebax and urethane. The device such as polypropylene, low density polyethylene (LDPE), high density polyethylene (HDPE), ethylene vinyl acetate (EVA), nylon, polyester and polyethylene terephthalate ("PET"), may be prepared through free blowing in a mold or inside a coil. Tubing is extruded with relatively thin walls and then free-blown in a mold, coil or other fixture to form the ribs/corrugation.

A balloon 14 for use according to the present invention may be any conventional balloon for catheter delivery, such as a balloon of the type generally used for PTA and PTCA procedures. Typically, balloon 14 is fixed at its distal end to inner shaft 12 near the catheter distal end and at its proximal end to inner shaft 12, near the distal end of the outer shaft 13. Balloon 14 is inflatable through an inflation conduit 23, i.e., the space between coaxial inner shaft 13 and outer shaft 13 of the catheter. The distal and proximal ends of balloon 14 are shown in FIGS. 1 and 2 positioned exterior to the distal and proximal ends of tube component 16, respectively, and of a length L-B generally equal to the length L-T of the tube component 16. To be compatible with the tube component 16 illustrated in FIGS. 1 and 2 and described above, balloon 14 is inflatable at deployment to about the diameter of the body vessel in which the stent 18 is to be deployed. Balloon 14 may be formed of a compliant or non-compliant material, such as polyethylene or any standard balloon material. Compliant materials include low pressure, relatively soft or flexible polymeric materials, such as thermoplastic polymers, thermoplastic elastomers, polyethylene (high density, low density, intermediate density, linear low density), various co-polymers and blends of polyethylene, ionomers, polyesters, polyurethanes, polycarbonates, polyamides, poly-vinyl chloride, acrylonitrile-butadiene-styrene copolymers, polyether-polyester copolymers, and polyetherpolyamide copolymers. Suitable materials include a copolymer polyolefin material available from E.I. DuPont de Nemours and Co. (Wilmington, Del.), under the trade name Surlyn™ Ionomer and a polyether block amide available under the trade name PEBAX™. Non-compliant materials include relatively rigid stiff high pressure polymeric materials, such as thermoplastic polymers and thermoset polymeric materials, poly(ethylene terephthalate) (commonly referred to as PET), polyimide, thermoplastic polyimide, polyamides, polyesters, polycarbonates, polyphenylene sulfides, polypropylene and rigid polyurethanes, or combinations thereof. The balloon 14 typically has a wall thickness of about 0.0007–0.004" for example.

A stent for use according to the present invention may be any conventional type of balloon expandable stent, including stents of the type used for PTA and PTCA angioplasty procedures, for prostate therapy, and TTS endoscopic catheters for gastrointestinal use. Suitable stent material is biocompatible stainless steel in the form of sheet metal, tube component wire or Nitinol. A preferred stent is described in PCT Application No. 960 3072 A1, published Feb. 8, 1996, the content of which is incorporated herein by reference. All such stents are well-known in this art generally and additional examples are described in U.S. Pat. No. 5,507,768 to Lau et al.; in U.S. Pat. No. 5,458,615 to Klemm et al.; in U.S. Pat. No. 5,226,899 to Scheiban; in U.S. Pat. No. 4,875,480 to Imbert; in U.S. Pat. No. 4,848,343 to Wallsten et al.; and in U.S. Pat. No. 4,733,665 to Palmaz. Stent 18 as shown in FIGS. 1 and 2 is positioned on balloon 14, which is over the underlying tube component 16, at the distal end of the catheter. The length L-S of stent 18 is shown as essentially equal or slightly smaller than the length L-T of tube component 16 and is positioned on assembly 10 to be coextensive with tube component 16. In this position, stent 18 is shown in FIG. 1 crimped to its delivery diameter D1, which is about 0.035–0.45" for example.

As discussed above, despite the most careful and firm crimping of stent 18 to closely conform to the overall profile of the catheter unexpanded balloon 14 and underlying tube component 16, there is a certain amount of "recoil" of stent 18 or a tendency of stent 18 to slightly open from a desired hypothetical minimum crimped diameter. The actual minimum diameter achievable for fully crimped stent 18 on assembly 10 is referred to as stent 18 delivery diameter D1. This tendency of stent 18 to open or recoil slightly when crimped on assembly 10 has been characterized as "recoil crimping". In FIG. 1, tube component 16 is shown at a diameter which is generally sufficient to compensate for any slack or looseness between crimped stent 18 and the overall profile of the catheter, the unexpanded balloon 14 and the underlying tube component 16 due to recoil crimping.

FIG. 2 illustrates a side profile section showing a stent delivery and deployment assembly 10 of this invention with balloon 14 fluid inflated to its fully expanded position. As a result of the fluid inflation of the balloon 14, stent 18 has also been fully expanded to its deployment diameter D2 in which it can be deployed against the walls of a body vessel in which it is situated.

Figure 3:
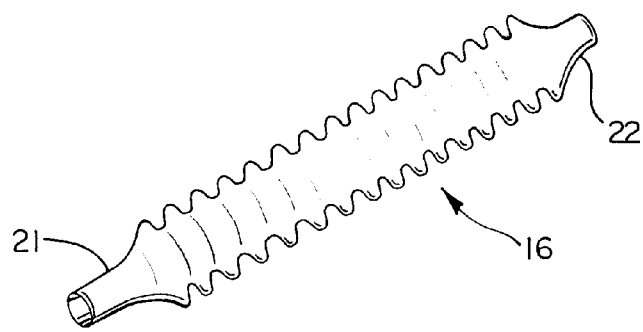
FIG. 3 is a perspective view of the corrugated tubing of the present invention.

FIG. 3 illustrates the preferred configuration of the tube component 16. The tube component has a plurality of ribs 30 and is configured in a corrugated or accordion fashion. The ends of the tube component 16, 22 and 21, are substantially rib-free so as to provide a flat surface to receive an adhesive and thereby bond to the inner shaft 12. Preferable adhesives include cyanocrylates such as Loctite 4061/4011 or urethanes, such as H. B. Fuller 3507/3506. The tube component may also be heat bonded to the inner shaft. The ribs may vary in frequency and spacing.

Figure 4:
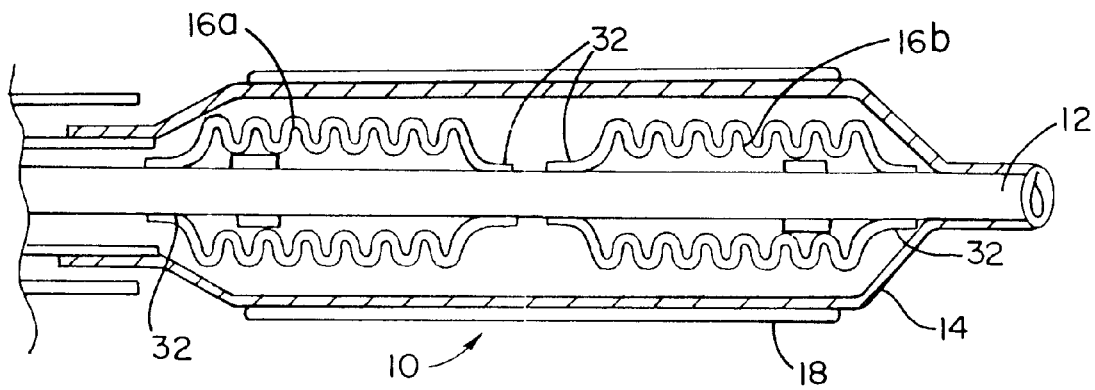
FIGS. 4–6 are side profile sections showing alternative embodiments of balloon expandable stent delivery and deployment assemblies, having the tubing component formed in a plurality of sections.
Figure 5:
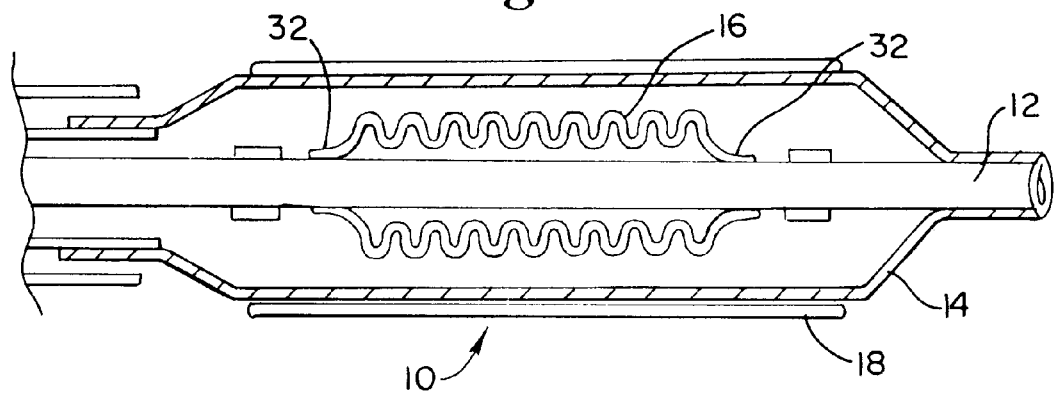
Figure 6:
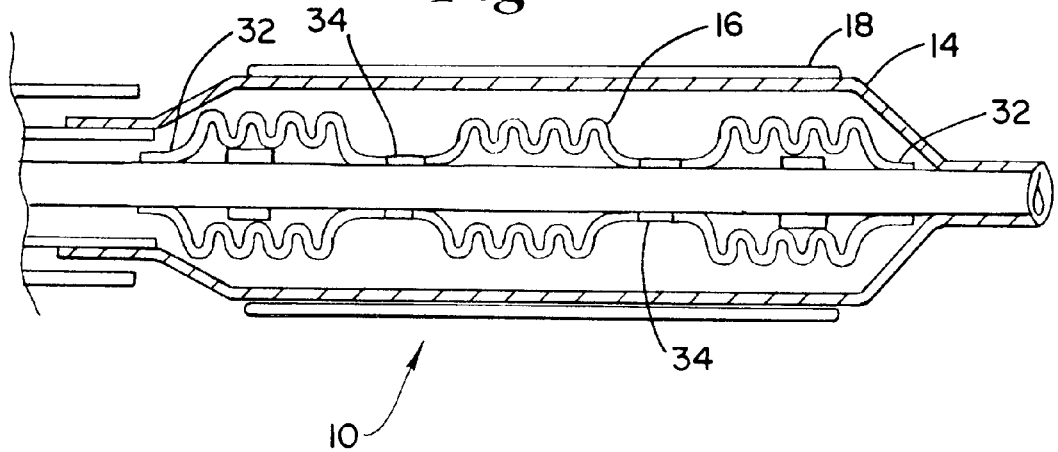

Tube component 16 may have different configurations in other embodiments, as shown in FIGS. 4–6. The tube component 16 may be comprised of more that one piece of corrugated tubing (FIG. 4), a smaller single piece (FIG. 5) or one single piece of tubing sectioned into a plurality of ribbed sections, wherein the tubing is adhered to the inner shaft 12 in more than two locations (FIG. 6).

FIG. 4 shows two pieces of tubing component 16a, 16b. Both pieces are adhered to inner shaft 12 at adhesion points 32. FIG. 5 discloses an embodiment which comprises one smaller piece of tube component 16 which is adhered to inner shaft 12 at adhesion points 32. FIG. 6 discloses an embodiment which comprises one tube component 16 which has interrupted ribbed sections 34 adhered to the inner shaft 12.

Figure 7:
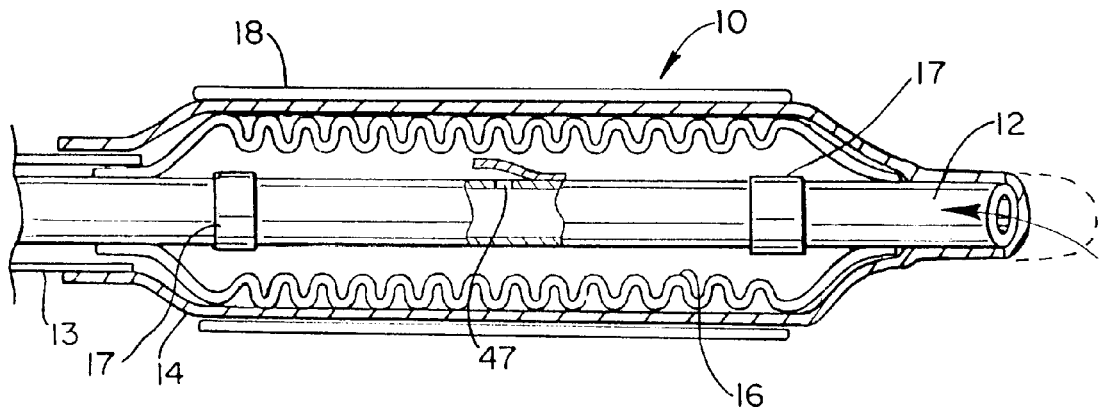
FIGS. 7–8 are side profile sections showing alternative embodiments of the balloon expandable stent delivery and deployment assemblies, the tube component inflatable to add securement pressure.
Figure 8:
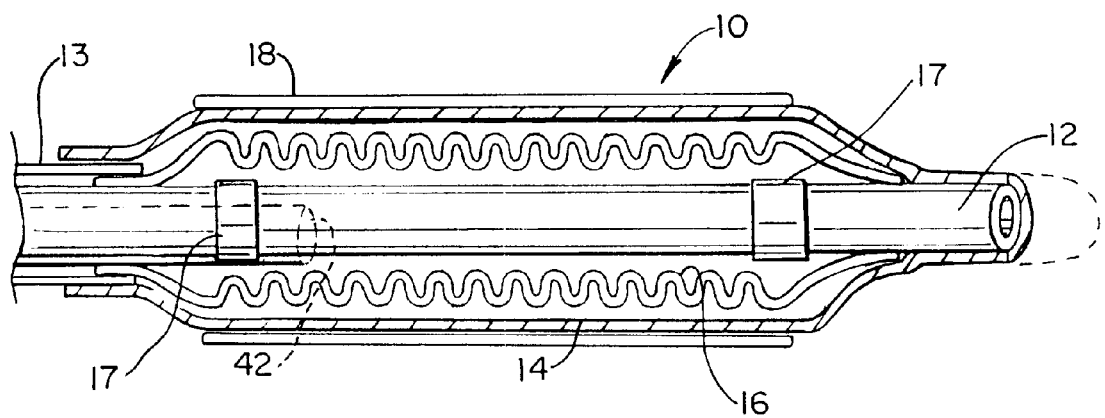

FIGS. 7 and 8 illustrate an alternative embodiment in which the tubing component is inflatable to increase the securement pressure on the inside of balloon 14 when the stent is crimped onto the balloon so as to negated additional recoiling. The full expansion of the tube component 16 should only be slightly greater than the diameter of the inside of the balloon 14 when the stent 18 is fully crimped onto the balloon 14.

In FIG. 7, the inflating fluid comes through the guide wire lumen 12 under pressure from the proximal end or the distal end of the guide wire lumen 12, preferably via a syringe, and fills the tubing component 16 through a one-way valve 47 (preferably resisting up to about 4 atm) in the inner catheter 12.

In FIG. 8, the tubing component 16 is inflated via an additional lumen 42 which extends from the proximal end of the catheter along the guide wire lumen 40, much the same as any inflating lumen incorporated to inflate a balloon.

Figure 9:
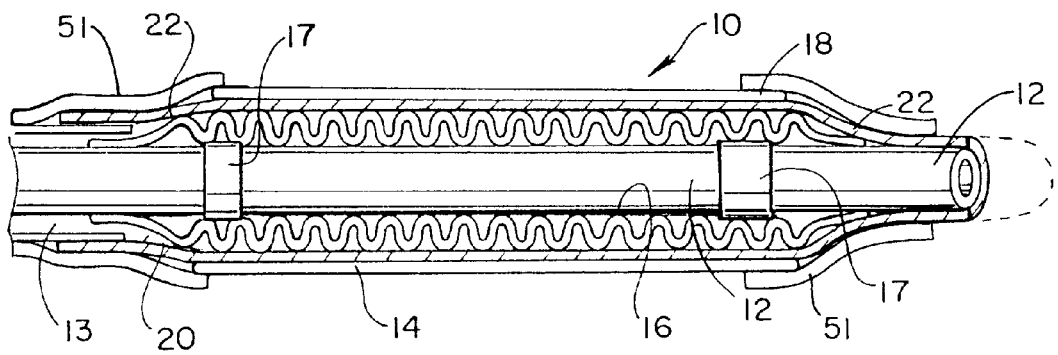
FIG. 9 is a side profile section showing a balloon expandable stent delivery and deployment assembly, with the stent crimped to delivery diameter onto the balloon, the underlying tube component and the catheter, and also having containment sleeves covering the ends of the stent.

In an alternative embodiment, as shown in FIG. 9, socks or sleeves 51 may be incorporated to stretch over the ends of the stent to prevent snagging and to secure the stent onto the balloon. Such sleeves are demonstrated in U.S. application Ser. Nos. 08/702,149, filed Aug. 23, 1996, and 08/701,979, filed Aug. 23, 1996, which are incorporated in their entirety herein by reference.

Figure 10:
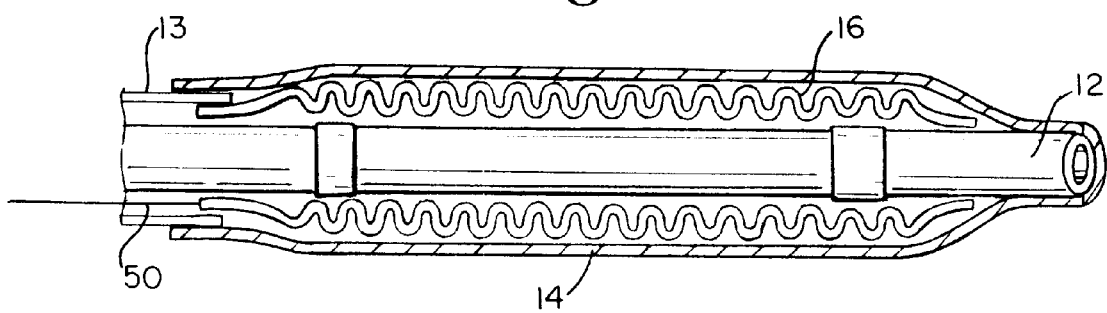
FIG. 10 is a side profile section showing a balloon expandable stent delivery and deployment assembly, with the stent crimped to delivery diameter onto the balloon, the underlying tube component and the catheter, and also having a pull-back wire attached to the tube component.

In still another embodiment, as shown in FIG. 10, the tubing component 16 is slidable axially along the inner shaft 12 and is connected to a retracting wire 50 such that the tubing component may be retracted into the outer shaft 13 after the balloon has been inflated to reduce the profile of the balloon 14 when the catheter is removed. The tubing component, since it is not adhered to the inner shaft 12 in this embodiment, should fit tightly enough on the inner shaft to stay in place, but not too tightly so that it may be retracted by pulling on the retracting wire 50.

The method of using the stent delivery and deployment assembly 10 of this invention, as shown in FIGS. 1 and 2, is described as follows. The assembly 10 is constructed as described above. Stent 18 is compressed or crimped onto balloon 14, tube component 16 and the catheter to a delivery diameter D1. This crimping can be done manually or with the aid of tooling specifically designed for the purpose either by the physician or the manufacturer. In the crimped position, stent 18 closely conforms to the overall profile of balloon 14, tube component 16 and the catheter except for the slight slack or looseness due to recoil crimping. Tube component 16 is flexible enough to slightly collapse during crimping and rebound to the extent necessary to compensate for the slack or looseness due to recoil crimping, thus securing the stent. As a result, the stent does not move out of its position on the catheter during delivery or become separated from the catheter within a body vessel. The catheter distal end is delivered by standard techniques to the deployment site within the body vessel of interest. At this point, stent 18 is positioned as required by the physician and balloon 14 is fluid inflated by standard technique to expand stent 18 to its deployment diameter D2. During this expansion, stent 18 is expanded to fill the body vessel.

Following deployment of stent 18, balloon 14 is deflated and the assembly is retracted proximally and withdrawn from the body. If required by the procedure, the site of entry to the body is appropriately closed.

The tube component provided by this invention increases stent securement force by increasing the frictional force between the tube component, the balloon wall and the internal diameter of the stent in its reduced crimped delivery diameter. The tube component is more flexible than a solid sheath under the expandable balloon, and thus the entire assembly has greater flexibility. This invention has particular advantages for assemblies in which the stent is provided for use as pre-crimped to the balloon and underlying catheter, by increasing the shelf life of the pre-crimped assembly. The tube component also protects the balloon material during crimping by acting as a buffer between the balloon material and whatever may be mounted on the inner shaft, such as marker bands 17. The features and principles described for this invention are suitable for use with fixed wire, over-the-wire and single operator exchange assemblies.

Another embodiment of the present invention is shown in FIGS. 11 and 12 which illustrate a side profile section showing an inflation expandable stent delivery and deployment assembly generally designated 110. Assembly 110 includes a catheter comprised of inner shafts 112 and 113 and an outer shaft 115 of the coaxial type, an inflation expandable balloon 114, an inflation tube component 116 such as an inner balloon and inflation expandable stent 118. Any conventional type of catheter may be used, such as a catheter of the type generally used for PTA or PTCA angioplasty procedures, for prostate therapy, and TTS endoscopic catheters for gastrointestinal use. However, coaxial types as shown are most preferred. The particular catheter 112 shown is formed of a biocompatible and hydrophilic compatible material, such as a lubricous polyimide or polyethylene. Other suitable materials for the catheter 112 include nylons, urethanes, and polypropylene materials compatible with coatings such as silicone and/or hydrophilic coatings. In addition to hydrophilic compatible materials, any biocompatible material may be used. For example, polyethylene or polypropylene can be coated with a hydrophilic material to render them hydrophilic compatible. suitable catheters for use according to the present invention include a number of catheters available from Scimed Life Systems, Inc., Maple Grove, Minn., the assignee of the present invention, such as BANDIT™, COBRA™, VIVA™, and VIVA PRIMO™ catheters.

Inflatable tube component 116 is fixed at its distal and proximal end to inner shaft 112 and at its proximal end to inner shaft 113 at a position to be encompassed within the distal and proximal ends of the outer balloon 114. According to art-recognized convention, the length L-B of the balloon 114 is defined as the length of the body portion of the balloon 114, excluding the terminal cone sections 120. As seen in FIG. 12, the body portion of the balloon 114 is generally cylindrical when in its deployed or inflated condition. Tube component 116 is illustrated as having terminal sections 122 which are more relatively vertical than the cone sections 120 illustrated for the balloon 114. However, it is to be understood that, according to the present invention, either of the terminal sections 120, 122 may be relatively cone shaped, relatively vertical or of any other configuration known to those of skill in this art. A preferred length L-T of the tube component 116 is illustrated in FIGS. 11 and 12 as substantially equal to the length L-B of balloon 114, and substantially equal to the length L-S of stent 112. However, according to the present invention, stent 112 should be supported by the underlying tube component 116 for a length sufficient to permit accomplishment of the stated purpose of the tube component 116, when inflated, to provide securement pressure for stent 112 to maintain stent 112 in position with assembly 110 during delivery. It is also within the present invention for tube component 116 to be slightly shorter than stent 112, for example, the distal end 119 of stent 112 may extend distally beyond the distal end 121 of tube component 116 (not shown), so that the distal end 119 of stent 121 can be crimped over the distal end 121 of tube component 116 to prevent the distal end 119 of stent 112 from catching and tending to further open as it is maneuvered within a body vessel. As has been explained above, tube component 116 is designed and constructed to be inflatable to no more than is necessary to compensate for recoil crimping of stent 112 and to closely accommodate (or even slightly over-stress) the delivery diameter of stent 112, taking into consideration the thickness of the intervening uninflated balloon 114. Tube component 116 is inflated through the opening(s) 117 of inner shaft 112. Typically, tube component 116 will have a wall thickness of about 0.0002–0.0007 inch and will be inflatable to no more than about 0.035.–0.045 inches.

Inflating tube component 116 may be formed of either compliant or non-compliant balloon materials. Compliant materials include low pressure, relatively soft or flexible polymeric materials, such as thermoplastic polymers, thermoplastic elastomers, polyethylene (high density, low density, intermediate density, linear low density), various co-polymers and blends of polyethylene, ionomers, polyesters, polyurethanes, polycarbonates, polyamides, poly-vinyl chloride, acrylonitrile-butadiene-styrene copolymers, polyether-polyester copolymers, and polyether-polyamide copolymers. Suitable materials include a copolymer polyolefin material available from E.I. DuPont de Nemours and Co. (Wilmington, Del.), under the trade name Surlyn™ Ionomer and a polyether block amide available under the trade name PEBAX™. Non-compliant materials include relatively rigid of stiff high pressure polymeric materials, such as thermoplastic polymers and thermoset polymeric materials, poly(ethylene terephthalate) (commonly referred to as PET), polyimide, thermoplastic polyimide, polyamides, polyesters, polycarbonates, polyphenylene sulfides, polypropylene and rigid polyurethanes.

A balloon 114 for use according to the present invention may be any conventional balloon for catheter delivery, such as a balloon of the type generally used for PTA and PTCA procedures. Typically, balloon 114 is fixed at its distal end to inner shaft 112 near the catheter distal end and at its proximal end to outer shaft 115. Balloon 114 is larger in diameter than tube component 116, because balloon 114 must be able to expand to a larger diameter than tube component 116. Balloon 114 is inflatable through an inflation conduit 123, i.e., the space between coaxial inner shaft 113 and outer shaft 115 of the catheter. The distal and proximal ends of balloon 114 are shown in FIGS. 11 and 12 positioned exterior to the distal and proximal ends of tube component 116, respectively, and of a length L-B generally equal to the length L-T of the tube component 116. To be compatible with tube component 116 illustrated in FIGS. 11 and 12 and described above, balloon 114 is inflatable at deployment to about the diameter of the body vessel in which the stent 118 is to be deployed. Balloon 114 may be formed of a compliant or non-compliant material, of the types of compliant materials described herein above, such as polyethylene or any standard balloon material. Balloon 114 typically has a wall thickness of about 0.0007–0.004 inch for example.

A stent for use according to the present invention may be any conventional type of balloon expandable stent, including stents of the type used for PTA and PTCA angioplasty procedures, for prostate therapy, and TTS endoscopic catheters for gastrointestinal use. Suitable stent material is biocompatible stainless steel in the form of sheet metal, tube component wire or Nitinol. A preferred stent is described in PCT Application No. 960 3072 A1, published Feb. 8, 1996, the content of which is incorporated herein by reference. All such stents are well known in this art generally and additional examples are described in U.S. Pat. No. 5,507,768 to Lau et al.; in U.S. Pat. No. 5,458,615 to Klemm et al; in U.S. Pat. No. 5,226,889 to Sheiban; in U.S. Pat. No. 4,875,480 to Imbert; in U.S. Pat. No. 4,848,343 to Wallsten et al., and in U.S. Pat. No. 4,733,665 to Palmaz. Stent 118 as shown in FIGS. 11 and 12 is positioned on balloon 114, the underlying inflatable tube component 116 and the distal end of the catheter. The length L-S of stent 118 is shown as essentially equal or slightly smaller than the length L-T of tube component 116 and is positioned on assembly 110 to be co-extensive with tube component 116. In this position, stent 118 is shown in FIG. 11 crimped to its delivery diameter D1, which is about 0.035–0.045 inch for example.

As discussed above, despite the most careful and firm crimping of stent 118 to closely conform to the overall profile of the catheter unexpanded balloon 114 and underlying inflatable tube component 116, there is a certain amount of "recoil" of stent 118 or a tendency of stent 118 to slightly open from a desired hypothetical minimum crimped diameter. The actual minimum diameter achievable for fully crimped stent 118 on assembly 110 is referred to as the stent 118 delivery diameter D1. This tendency of stent 118 to open or recoil slightly when crimped on assembly 110 has been characterized as "recoil crimping". In FIG. 11, inflatable tube component 116 is shown inflated to a diameter which is generally sufficient to compensate for any slack or looseness between crimped stent 118 and the overall profile of the catheter, the unexpanded balloon 114 and the underlying inflatable tube component 116 due to recoil crimping.

FIG. 12 illustrates a side profile section showing a stent delivery and deployment assembly 110 of this invention with balloon 114 fluid inflated to its fully expanded position. As a result of the fluid inflation of the balloon 114, stent 118 has also been fully expanded to its deployment diameter D2 in which it can be deployed against the walls of a body vessel in which it is situated.

Tube component 116 may have a shape other than the cylindrical shape described and illustrated with regard to the embodiment shown in FIGS. 11 and 12. Further, the tube component may be comprised of more than one separately inflatable pouch. For example, as illustrated with regard to FIG. 13, the tube component of an alternative stent delivery and deployment assembly generally designated 130 can be comprised of three separately inflatable pouches 136, 138, 140. The pouches 136, 138, 140 are each separately inflatable through their respective inflation conduits 137, 139, 141, and each of the pouches 136, 138, 140 can be inflatable to a different extent. The conduits are formed in the wall of shaft 132 as can be seen in FIGS. 14–16. The stent delivery and deployment assembly 130 of FIG. 13 is also comprised of a catheter having inner shaft 132 and outer shaft 135, a balloon 134, with its balloon inflation conduit 139 and the balloon terminal cone sections 144, and a stent 142. As has been explained above with reference to FIGS. 11 and 12, stent 142 is crimped to closely conform to the overall profile of the catheter the unexpanded balloon 134 and the underlying inflatable pouches 136, 138 140. Even with the most careful and firm crimping, there is a certain amount of "recoil" of the stent 142 or a tendency of stent 142 to slightly open from a desired hypothetical minimum diameter. In FIG. 13, the first 136 and third 140 pouches are inflated to a slightly larger size than the second pouch 138. As discussed above, the inflation of the pouches 136, 138, 140 to this configuration is generally sufficient to compensate for any slack or looseness between the crimped stent 142 and the overall profile of the catheter, the unexpanded balloon 134 and the underlying inflatable pouches 136, 138, 140 due to recoil crimping. Once pouches 136, 138 140 have been inflated to the configuration shown in FIG. 13, stent 142 is firmly secured against axial movement with regard to assembly 130. The distal 146 and proximal 148 ends of stent 142 are protected from any possible unwanted contact with vessel walls during maneuvering, which helps to protect the vessel walls from abrasion and also helps to protect the ends 146, 148 of stent 142 from distortion. Additionally, stent 142 may be of a length such that it fits over pouch 140 and pouch 136 as well as over pouch 138.

The method of using the stent delivery and deployment assembly 110 of this invention, as shown in FIGS. 11 and 12, is described as follows. The assembly 110 is constructed as described above. Stent 118 is compressed or crimped onto balloon 114, inflatable tube component 116 and the catheter to a delivery diameter D1. This crimping can be done manually or with the aid of tooling specially designed for the purpose either by the physician or the manufacturer. In the crimped position, stent we closely conforms to the overall profile of balloon 114, inflatable tube component 116 and the catheter except for the slight slack or looseness due to recoil crimping. Tube component 116 is fluid inflated to the extent necessary to compensate for this slack or looseness due to recoil crimping. The pressure of force required to inflate tube component 116 to this extent is also referred to as securement pressure, i.e., the force or pressure needed to secure stent 112 in this position. It is to be noted that, since tube component 116 is designed and constructed to be capable of fully expanding to no more than the size necessary to compensate for recoil crimping, there is no possibility of stent 112 expanding or beginning to open to a larger diameter. Thus, there is no hazard of stent 112 moving out of its position on the catheter during delivery or of becoming separated from the catheter within a body vessel. The catheter distal end is delivered by standard techniques to the deployment site within the body vessel of interest. At this point, stent 112 is positioned as required by the physician and balloon 114 is fluid inflated by standard technique to expand stent 121 to its deployment diameter D2. During this expansion, stent 112 is expanded to fill the body vessel. Following deployment of stent 112, balloon 114 and optionally, tube component 116 are deflated and the assembly 110 is retracted proximally and withdrawn from the body. If required by the procedure, the site of entry to the body is appropriately closed.

The method of using the stent delivery and deployment assembly 130 of this invention, as shown in FIG. 13, is similarly described. The assembly 130 is constructed as described above. Stent 142 is compressed or crimped to closely conform to the overall profile of balloon 134, inflatable pouches 136, 138, 140 and the catheter except for the slight slack or looseness due to recoil crimping. Pouches 136, 138, 140 are each fluid inflated to the profile shown in FIG. 13 through separate fluid inflation conduits (not shown) to securement pressure to compensate for this slack or looseness and to secure stent 142 in this position. The overall configuration of pouches 136, 138 140 further serves to position stent 142 against axial dislocation during delivery. The catheter is delivered by standard techniques to the deployment site within the body vessel of interest. At this point, stent 142 is positioned as required by the physician and balloon 134 is fluid inflated by standard technique to expand and deploy stent 142. Following deployment of stent 142, balloon 134 and, optionally, pouches 136, 138 140 are deflated and the assembly 130 is retracted proximally and withdrawn form the body. If required by the procedure, the site of entry to the body is appropriately closed.

The inflation tube component provided by this invention also maximizes stent securement force by optimizing the frictional force between the inflating tube component, the balloon wall and the internal diameter of the stent in its reduced crimped delivery diameter. The inflation tube component is more flexible than a solid sheath under the expandable balloon, and thus the entire assembly has greater flexibility. This invention has particular advantages for assemblies in which the stent is provided for use as pre-crimped to the balloon and underlying catheter, by increasing the shelf life of the pre-crimped assembly. The features and principles described for this invention are suitable for use with fixed wire, over-the-wire and single operator exchange assemblies.

It should be understood that the various elements and materials of all embodiments could be utilized in each of the other embodiments if desired.

The above examples and disclosures are intended to be illustrative and not exhaustive. These examples and descriptions will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is as follows:

1. An assembly for delivery and deployment of an inflation expandable stent within a vessel, comprising:
a catheter having proximal and distal ends and an inner shaft;
an expandable balloon coaxially mounted on the catheter, the balloon having an expanded state and a collapsed state; and
a tube component coaxially mounted on the catheter axially within the expandable balloon, the tube component having a certain length and forming a continuous covering over the inner shaft along the tube's length and the tube component having an expanded state, wherein the tube component is capable of being in its expanded state while the balloon is in its collapsed state.

2. The assembly according to claim 1, the tube component having a plurality of ribs, the assembly further comprising a stent, inflation expandable from a delivery diameter to a deployment diameter, such that the delivery diameter is reduced from the deployment diameter for conforming the stent to the catheter, such that the stent, in its delivery diameter, is coaxially mounted on the catheter near the catheter distal end, the expandable balloon being capable of expansion of the stent from the delivery diameter to the deployment diameter upon application of fluid deployment pressure to the balloon.

3. The assembly according to claim 2, wherein the tube component is a thermoplastic corrugated tube adhered to the inner shaft and is formed from a low modulus polymer.

4. The assembly according to claim 3, the tube component being formed from a material chosen from the group consisting of polypropylene, low density polyethylene (LDPE), high density polyethylene (HDPE), ethylene vinyl acetate (EVA), nylon, polyester, polyethylene terephthalate ("PET"), Surlyn™, Pebax and urethane.

5. The assembly according to claim 3, wherein the diameter of the tube component is approximately equal to the delivery diameter of the stent.

6. The assembly according to claim 5, wherein the tube component is essentially equal in length to the stent and wherein the stent is positioned on the assembly essentially coextensive with the tube component.

7. The assembly according to claim 2, wherein the tube component is inflatable, such that when the tube component is inflated it applies radial pressure on the expandable balloon, when the stent is in its delivery diameter.

8. A method for delivering and deploying a stent using an assembly according to claim 2, comprising:
    providing a catheter having proximal and distal ends, with an expandable balloon coaxially mounted on the catheter, and a tube component having a plurality of ribs coaxially mounted on the catheter, axially within the expandable balloon, so that the balloon is in an unexpanded condition;
    providing a stent which is expandable from a delivery diameter to a deployment diameter;
    mounting the stent, in a diameter greater than the delivery diameter, on the balloon;
    contracting the stent to the delivery diameter to conform to an overall profile of the catheter, the tube component and the balloon;
    delivering the assembly to a deployment site; and
    inflating the balloon to expand the stent to its deployment diameter.

9. The method according to claim 8, wherein the tube component is a corrugate tubing adhered to the catheter formed of a low modulus polymer and having a diameter of approximately that of the delivery diameter.

10. The method according to claim 8, wherein the tube component is essentially equal in length to the stent and wherein the stent is positioned on the assembly essentially coextensive with the tube component.

11. An assembly for delivery and deployment of an inflation expandable stent within a vessel, comprising:
    a catheter having proximal and distal ends and an inner shaft;
    an expandable balloon coaxially mounted on the catheter;
    a tube component coaxially mounted on the catheter axially within the expandable balloon, the tube component having a plurality of ribs and wherein the tube component is comprised of more than one corrugated tube; and
    a stent, inflation expandable from a delivery diameter to a deployment diameter, such that the delivery diameter is reduced from the deployment diameter for conforming the stent to the catheter, such that the stent, in its delivery diameter, is coaxially mounted on the catheter near the catheter distal end, the expandable balloon being capable of expansion of the stent from the delivery diameter to the deployment diameter upon application of fluid deployment pressure to the balloon.

12. The assembly according to claim 6, further comprising marker bands fixed to the inner shaft beneath the tube component.

13. An assembly for delivery and deployment of an inflation expandable stent within a vessel, comprising:
    a catheter having proximal and distal ends and an inner shaft;
    an expandable balloon coaxially mounted on the catheter;
    a tube component coaxially mounted on the catheter axially within the expandable balloon, the tube component having a plurality of ribs; and
    a stent, inflation expandable from a delivery diameter to a deployment diameter, such that the delivery diameter is reduced from the deployment diameter for conforming the stent to the catheter, such that the stent, in its delivery diameter, is coaxially mounted on the catheter near the catheter distal end, the expandable balloon being capable of expansion of the stent from the delivery diameter to the deployment diameter upon application of fluid deployment pressure to the balloon,
    the assembly further comprising at least one sleeve having first and second ends, the first end being attached to the catheter and the second end covering a portion of the stent, when the stent is in its delivery diameter.

14. The assembly according to claim 13, comprising two sleeves, one covering each end of the stent, when the stent is in its delivery diameter.

15. An assembly for delivery and deployment of an inflation expandable stent within a vessel, comprising:
    a catheter having proximal and distal ends and an inner shaft;
    an expandable balloon coaxially mounted on the catheter;
    a tube component coaxially mounted on the catheter axially within the expandable balloon, the tube component having a plurality of ribs; and
    a stent, inflation expandable from a delivery diameter to a deployment diameter, such that the delivery diameter is reduced from the deployment diameter for conforming the stent to the catheter, such that the stent, in its delivery diameter, is coaxially mounted on the catheter near the catheter distal end, the expandable balloon being capable of expansion of the stent from the delivery diameter to the deployment diameter upon application of fluid deployment pressure to the balloon,
    wherein the tube component is slidable along the inner shaft and is attached to a retracting means, such that after the stent has been deployed, the user may slide the tube component proximally along the inner shaft.

16. An assembly for delivery and deployment of an inflation expandable stent within a vessel, comprising:
    a catheter having proximal and distal ends and an inner shaft;
    an expandable balloon coaxially mounted on the catheter; and
    a tube component coaxially mounted on the catheter within the expandable balloon, wherein the tube component is an expandable tube component coaxially mounted on the catheter, axially within the expandable balloon, the tube component designed and adapted for fluid expansion to provide a securement pressure to the stent in the delivery diameter to maintain the stent in position on the catheter during delivery to the deployment site, the assembly further comprising a stent, inflation expandable from a delivery diameter to a deployment diameter, such that the delivery diameter is reduced from the deployment diameter for conforming the stent to the catheter, such that the stent, in its delivery diameter, is coaxially mounted on the catheter near the catheter distal end.

17. The assembly according to claim 16, wherein the expandable tube component is sized and constructed to be fluid expandable to no more than the delivery diameter and to no more than the securement pressure.

18. The assembly according to claim 16, wherein the tube component is essentially equal in length to the stent and wherein the stent is positioned on the assembly essentially coextensive with the tube component.

19. The assembly according to claim 17, wherein the tube component is comprised of more than one inflatable pouch.

20. The assembly according to claim 19, wherein the tube component is comprised of three pouches, with a proximal and distal pouch inflatable to a greater pressure than a medial pouch.

21. A method for delivering and deploying a stent using an assembly according to claim 16, comprising:

providing a catheter having proximal and distal ends, with an expandable balloon coaxially mounted on the catheter, and an expandable tube component coaxially mounted on the catheter, axially within the expandable balloon, so that the balloon and the tube component are each in an unexpanded condition;

providing a stent which is expandable from a delivery diameter to a deployment diameter;

mounting the stent, in a diameter greater than the delivery diameter, on the balloon;

contracting the stent to the delivery diameter to conform to an overall profile of the catheter, the tube component and the balloon;

inflating the tube component to provide to the stent a securement pressure to retain the stent in the delivery diameter;

delivering the assembly to a deployment site; and inflating the balloon to expand the stent to its deployment diameter.

22. The method according to claim 21, wherein the expandable tube component is sized and constructed to be fluid expandable to no more than the delivery diameter.

23. The method according to claim 21, wherein the tube component is essentially equal in length to the stent and wherein the stent is positioned on the assembly essentially coextensive with the tube component.

24. The method according to claim 21, wherein the tube component is comprised of more than one inflatable pouch.

25. The method according to claim 24, wherein the tube component is comprised of three pouches, with a proximal and distal pouch inflatable to a greater pressure than a medial pouch.

26. An assembly for delivery and deployment of an inflation expandable stent within a vessel, comprising:

a catheter having proximal and distal ends and an inner shaft;

a stent, inflation expandable from a delivery diameter to a deployment diameter, such that the delivery diameter is reduced from the deployment diameter for conforming the stent to the catheter, such that the stent, in its delivery diameter, is coaxially mounted on the catheter near the catheter distal end;

an expandable balloon coaxially mounted on the catheter axially; and a securement means for securing the stent to the balloon, the securement means coaxially mounted on the catheter axially within the expandable balloon.

27. The assembly of claim 26 wherein the securement means is an expandable tube component, the component designed and adapted for fluid expansion to provide a securement pressure to the stent in the delivery diameter to maintain the stent in position on the catheter during delivery to the deployment site.

28. The assembly of claim 26 wherein the securement means is a tube component coaxially mounted on the catheter axially within the expandable balloon, the tube component having a plurality of ribs.

\* \* \* \* \*